United States Patent [19]

Albert et al.

[11] Patent Number: 4,624,850
[45] Date of Patent: Nov. 25, 1986

[54] LIVE ATTENUATED HUMAN ROTAVIRUS VACCINE

[75] Inventors: Manuel J. Albert, Keilor; Graeme L. Barnes, Kew East; Ruth F. Bishop, Brighton, all of Australia

[73] Assignee: Royal Children's Hospital Research Foundation, Parkville, Australia

[21] Appl. No.: 699,717

[22] Filed: Feb. 8, 1985

[51] Int. Cl.$^4$ .............................................. A61K 39/12
[52] U.S. Cl. ..................................... 424/89; 435/237; 435/235
[58] Field of Search ................... 424/89; 435/237, 235

[56] References Cited

PUBLICATIONS

Babiuk et al. -Chem. Abst. vol. 88 (1978) p. 71141z.
Albert, M. J., et al., J of Clin Microbiol (1983) 17:162-164.
Babiuk, I. A., et al., J of Clin Microbiol (1977) 6:610-617.
Dyall-Smith, M. L., et al., Nucleic Acids Res (1984) 12:3973.
Faulkner-Valle, G. P., et al., J of Virol (1982) 42:669-677.
Bishop, R. F., et al., The Lancet (1974) Feb., pp. 149-151.
Kutsuzawa, T., et al., J of Clin Microbiol (1982) 16:727-730.
Laemmli, U. K., Nature (1970) 227:680-685.
Rodger, S. M., et al., J. Clin Microbiol (1981) 13:272-278.
Rodger, S. M., et al., "Comparison of the Genomes of Simian, Bovine and Human Rotaviruses by Gel Electrophoresis and the Detection of Genomic Variation Amongst Bovine Isolates" (in press).
Sato, K., et al., Archives of Virology (1981) 69:155-160.
Whitby, H. J., et al., J Clin Pathol (1980) 33:484-487.
Urasawa, T., et al., Microbiol Immunol (1981) 25(10):1025-1035.
Who Expert Comm. on Biological Standardization, 33rd Report (Technical Report Series 687), Who:-Geneva, 1983.

*Primary Examiner*—Sam Rosen
*Attorney, Agent, or Firm*—Ciotti & Murashige

[57] ABSTRACT

This invention provides a live attenuated human rotavirus vaccine and a method for the preparation of such a vaccine. The method overcomes problems experienced hitherto in the growth of human rotaviruses, by the use of larger quantities of inocula at the initial growth stage and subsequent passages.

3 Claims, 2 Drawing Figures

LIVE ATTENUATED HUMAN ROTAVIRUS VACCINE

The present invention relates to a live attenuated human rotavirus vaccine and to a method of producing such a vaccine. It also provides a method of prevention of acute diarrhoea caused by such human rotavirus.

BACKGROUND

Rotavirus particles were originally identified in 1974 in stool specimens by electron microscopy (Bishop et al, "Detection of a new virus by electron microscopy of faecal extracts from children with acute gastroenteritis." Lancet, 1974, 149).

Rotaviruses are now recognised as an important cause of severe acute diarrhoea in young children throughout the world. After the initial identification of rotaviruses as causative agents of actue diarrhoea, efforts were made to culture them in a wide variety of cell lines without much success.

Human rotaviruses have been broadly classified into two groups, those with "short RNA" (S) patterns and those with "long RNA" (L) patterns, based on the mobility of their RNA genome segments upon gel electrophoresis.

In 1981, Sato et al described successful cultivation of human rotaviruses from faecal specimens using roller cultures of MA-104 cells; "Isolation of human rotavirus in cell cultures." Arch. Virol. 69:155-160. Specimens were pretreated with trypsin and small amounts of trypsin were incorporated into the maintenance medium. The technique has been used successfully by others to culture rotavirus strains from diarrhoeal stools.

The majority of strains so far grown are those with the "L" patterns. "S" pattern strains have proved difficult to grow and successful cultivation of only two strains of rotavirus with "S" patterns has been described to date (for example, in 1982 by Kutsuzawa et al, "Isolation of human rotavirus subgroups 1 and 2 in cell culture." J. Clin. Microbiol. 16:727-730).

THE INVENTION

The inventors have succeeded in cultivating six human rotavirus strains of major epidemiological importance in Australia and in Papua New Guinea and in preparing live attenuated virus strains which show promise as a vaccine.

The strains that caused epidemics of diarrhoea in Melbourne, Australia during 1977-1979 and in Papua New Guinea in 1979 were both "S" pattern strains, but were of different electropherotypes. The inventors were successful in cultivating "S" pattern viruses from 2 of 6 stool specimens selected that contained "S" pattern viruses. Others have found "S" pattern strains difficult to cultivate.

The inventors used a modified procedure of cultivation as compared with the original procedure of Sato et al. 1.0 ml of stool filtrate was used for initiation of culture and 1.0 ml of tissue culture fluid for all subsequent passages. It is surprising that this increased amount of inoculum was successful as compared with the previous procedure. It is possible that increased numbers of infectious particles in the large inocula employed in the present study might have increased the chances of successful cultivation of strains with "S" patterns.

The inventors have successfully cultivated strains from whole faeces stored at −70° C., from faeces stored in PBS both at −20° C. and −70° C. and from sucrose cushion pelleted virus stored at −70° C. Since the number of strains cultivated is small, it is not yet possible to draw conclusions about the optimal storage conditions of faecal specimens for cultivation of virus.

The invention also provides a vaccine for providing immunological protection against acute diarrhoea caused by human rotavirus, which comprises either a live attenuated strain of the virus designated Hu/Australia/10-25-10/77/L being the subject of ATCC Deposit dated Feb. 1, 1985 or a live attenuated strain of the virus designated Hu/Australia/1-9-12/77/S being the subject of ATCC Deposit dated Feb. 1, 1985. Hu/Australia/10-25-10/77/L has ATCC identification number VR2104: Hu/Australia/1-9-12/77/S has an ATCC number R2105. The invention also provides a vaccine with enhanced cross-protection which comprises both live attenuated strains of the viruses defined previously.

DETAILED DESCRIPTION

Separation of rotavirus

Figure 1:
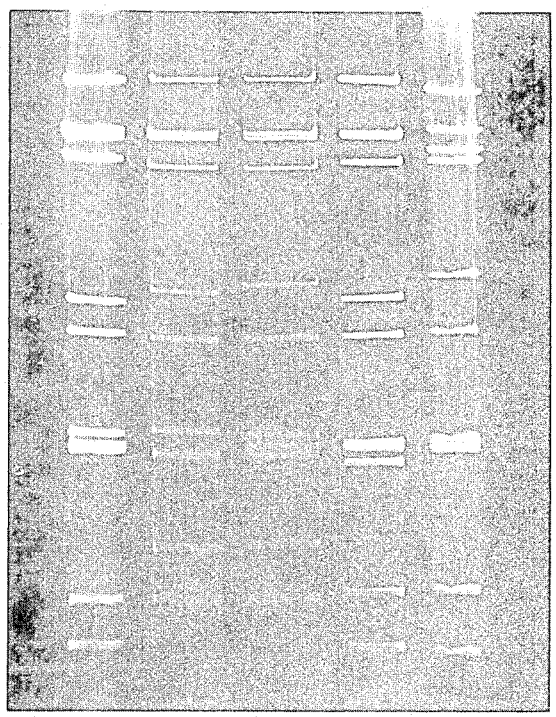
FIG. 1 shows the gel electrophoresis pattern of RNA obtained from cultured human rotaviruses, along with that of simian agent SA11.
Figure 2:
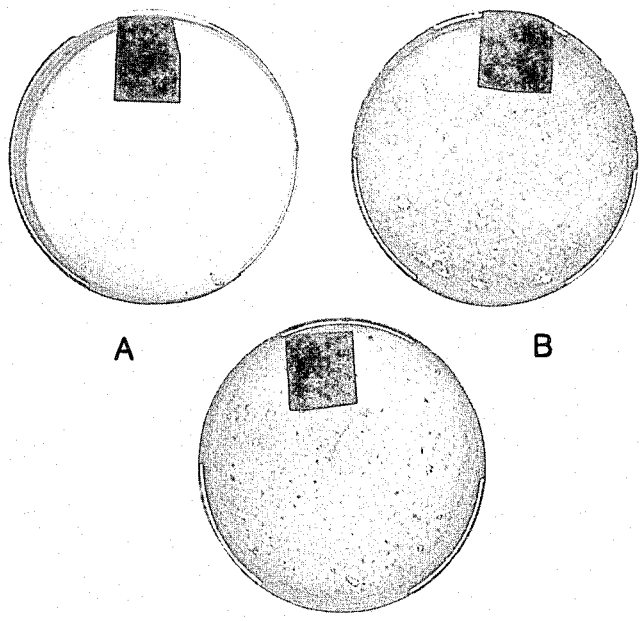
FIG. 2 shows plaques formation by uninfected cells (A), cells infected with RV-5 (B) and cells infected with RV-3 (C).

From 1973 onwards, the inventors have been storing rotavirus strains identified in faeces of children with acute diarrhoea. Most of these specimens were obtained from Australian children. In addition, the inventors used specimens obtained by collaborative epidemiological surveys conducted in Indonesia and in Papua New Guinea. Many of these stored strains had been examined by gel electrophoresis of genome RNA (for example, in 1981 by Rodger et al, "Molecular epidemiology of human rotaviruses in Melbourne, Australia, from 1973 to 1979, as determined by electrophoresis of genome ribonucleic acid." J. Clin. Mirobiol. 13:272-278).

Faecal specimens containing rotavirus particles of known electropherotypes were selected by the inventors. The objective was to cultivate human rotavirus strains that had caused major outbreaks of acute diarrhoea in children in Australia and elsewhere.

Specimens were stored either as whole faeces, 20% faecal homogenates in phosphate buffered saline (PBS, pH 7.0) or as sucrose cushion pelleted virus either at −70° C. or at −20° C. for varying periods.

The diarrhoeal stools selected for cultivation all contained a large number of predominantly double-shelled virus particles (2-4+ or greater than $10^8$ virus particles/ml under electron microscopy). The details of the specimens are as follows:

1. Eight stools containing "R electropherotype" (see Rodger et al above) collected during 1977 from children in a neonatal nursery of an obstetric hospital in Melbourne and stored as a 20% homogenate in PBS at −70° C.

2. Five stools containing "M electropherotype" (Rodger et al,) collected from children in Melbourne during 1977-1978 and stored either as a 20% homogenate in PBS, or as sucrose cushion pelleted virus at −70° C. (see the 1983 paper by Albert et al, "Epidemiology of rotavirus diarrhoea in the Highlands of Papua Nee Guinea, in 1979, as revealed by electrophoresis of genome RNA." J. Clin. Microbiol. 17:162–164)

3. One stool containing "PA electropherotype" collected from a child affected in a epidemic of rotavirus diarrhoea in the Highlands of Papua New Guinea during 1979 and stored as a 20% homogenate in PBS at −20° C.

4. One stool containing an "L" pattern rotavirus collected from a child affected in an epidemic of rotavirus diarrhoea in Queensland, Australia in 1981 and stored as whole faeces at −20° C.

5. One stool containing an "L" pattern rotavirus of the predominant electropherotype collected from a child in Melbourne in 1981 and stored as a 20% homogenate in PBS at −70° C.

Technique of culture (i) The technique of cultivation generally followed that of Sato et al. MA-104 cells (cell-line 104 distributed by Microbiological Associates (MA) Bioproducts, Walkerville, MA, USA) were grown in Dulbecco's modified medium (DMM, Flow Laboratories, Sydney, Australia, Cat. No. 74-013-54) with the addition of 10% foetal calf serum (FCS, Flow Laboratories, Sydney, Australia) and 12.5 $\mu$g/ml each of neomycin sulphate and polymyxin B sulphate. Three day old confluent monolayers of cells in culture tubes were used for the cultivation of the virus.

The faecal specimens containing rotavirus were thawed, and whole faecal samples homogenised to form a 20% suspension in PBS. All specimens were the vortexed and centrifuged at 3,000 g for 10 minutes. The supernatants were made bacteria-free by passing through 0.45 $\mu$m membrane filters (Millipore Corp., Bedford, MA, USA).

Inocula were pretreated with 10 $\mu$g/ml of trypsin (Sigma, trypsin 1X, Sigma Co., St. Louis, MO, USA). The maintenance medium (DMM) during virus multiplication contained 1 $\mu$g of trypsin per ml.

Virus concentrations in the inocula were checked by electron microscopy. The inocula were used only if concentrations of virus particles were greater than $10^8$ virus particles/ml.

1.0 ml aliquots of the faecal material treated with trypsin were inoculated into 2.0 ml cell cultures of MA 104 cells grown as confluent cell monolayers in roller tubes. Sato et al used 0.1 ml aliquots. Many subsequent attempts by others to culture other rotaviruses using 0.1 ml aliquots have failed. Use of 0.1 ml aliquots by the inventors also failed. The change to 1.0 ml aliquots led to success with the culture of several rotavirus strains.

Each specimen was inoculated into duplicate tubes. Cells from one tube were used for immunofluorescent staining for monitoring virus multiplication after each passage using rabbit antiserum against simian virus SA-11 and goat FITC-conjugated anti-rabbit IgG (goat immunoglobulin, conjugated with fluorescein isothiocyanate, distributed by Tago Inc, Burlingame, CA, USA). The other culture tube was used for the next passage. At each passage, 1.0 ml of undiluted material from the previous passage was used as inoculum. This feature may also be contrasted with the technique used by Sato et al.

Serial passages were performed until cytopathogenic effect (CPE) became evident. The culture fluid was then examined for virus by electron microscopy (see 1980 paper by Whitby et al, "Detection of virus particles by electron microscopy with polyacrylamide hydrogel." J. Clin. Pathol. 33:484–487).

(ii) F Rh L 2 cells (DBS-FRhL$_2$-2, distributed by ATCC, Rockville, Md., U.S.A.) were grown in minimal essential medicium (Eagle), to which was added non essential amino acids in Earles BSS (BME), 10% foetal calf serum (FCS, Flow Laboratories, Sydney, Australia) and 12.5 $\mu$g/ml each of neomycin sulphate and polymyxin B sulphate.

RV-3 virus, previously cultivated in MA-104 cells, was innoculated into seven day-old confluent monolayers of cells in small plastic flasks. The technique of cultivation then followed that described above. Serial passages were performed at 2–7 day intervals, and virus multiplication was monitored by enzyme immunoassay (EIA) and later by immunofluorescent staining.

Gel electrophoresis of RNA genome of virus

This has been described elsewhere (Rodger et al above). Briefly, stool specimen or cell culture fluid was disrupted with sodium dodecyl sulphate and deproteinised with a combination of phenol, chloroform and isoamyl alcohol. Electrophoresis of deproteinised RNA was carried out in 10% polyacrylamide slab gels using the discontinuous buffer system described by Laemmli in 1970 ("Cleavage of structural proteins during the assembly of the head of bacteriophage T4." Nature (London) 227:680–685.) The electropherotypes of all viruses were identified initially from stools and checked after appearance of CPE in cell culture, that is, cell damage produced by a virus growing in a layer of cells.

Plaquing of virus

After adaptation to stationary cell culture, the viruses were plaqued (see 1981 paper by Urasawa et al, "Sequential passages of human rotavirus in MA-104 cells." Microbiol. Immunol. 25:1025–1035) to measure the quantity of virus. The overlay consisted of 0.6% purified agar (Oxoid, England) and 2 $\mu$g/ml of trypsin. A second overlay containing neutral red (0.067 mg/ml) was applied 4 to 5 days after incubation.

RESULTS

Six human rotavirus strains were successfully adapted to cell culture out of 16 stool specimens studied. Three of these strains were isolated from stools stored in PBS at −70° C., one from sucrose cushion pelleted virus stored at −70° C., one from faeces stored in PBS at −20° C.and one from faeces stored at −70° C. Characteristic intracytoplasmic fluorescence was observed for these six strains from first passage until CPE appeared. One other strain showed initial fluorescence for 3 passages, but this subsequently disappeared. The remaining 9 specimens showed no intracytoplasmic fluorescence from first passage until tenth passage, at which stage, the viruses were judged uncultivable. For all the cultivable strains, CPE appeared between six and nine passages. It consisted of increased granularity, rounding into clusters and ultimate sloughing of cells 3 to 5 days after inoculation of a MA-104 cell monolayer. No difference in CPE was observed between various strains. Examination of cell culture fluids after the appearance of CPE showed mixtures of single and double-shelled virus particles.

The six cultured viruses are named herein using a modification of the nomenclature scheme first proposed in 1979 by Rodger and Holmes ("Comparison of genomes of simian, bovine and human rotaviruses by gel electrophoresis and detection of genomic variation among bovine isolates."J. Virol. 30:839–846). The scheme uses a cryptogram to contain the following information:

a. Species of animal from which the rotavirus was obtained.
b. Geographical origin of the virus.
c. Laboratory strain identification.
d. Year in which the virus was obtained.
e. Electropherotype pattern i.e. "S" or "L".

When reference sera for identification of serotype and sub-group are available, it will be possible to add this information to the cryptogram for each strain.

The cryptograms and new laboratory designations for the cultivated strains according to the invention are as follows:

| Cryptogram | Laboratory designation |
|---|---|
| 1. Hu/Australia/6-5-7/77/L | RV-1 |
| 2. Hu/Australia/11-20-9/77/L | RV-2 |
| 3. Hu/Australia/10-25-10/77/L | RV-3 |
| 4. Hu/Australia/6-6-1/81/L | RV-4 |
| 5. Hu/Australia/1-9-12/77/S | RV-5 |
| 6. Hu/Papua New Guinea/U25/79/S | RV-6 |

RV-1, RV-2 and RV-3 appear identical, and correspond to "R electropherotype", RV-5 to "M electropherotype" (Rodger et al above) and RV-6 to "PA electropherotype" (Albert et al above).

The RNA patterns (using the gel electrophoresis technique according to Rodger et al, described above) of cultured human rotaviruses according to the invention are shown in FIG. 1, along with the RNA pattern of simian agent. SA11, which was routinely grown in the laboratory. (From left to right are RV-1, RV-6, RV-5, RV-4 and SA-11. ) Coelectrophoresis of RNAs of the original stool viruses with the cell culture adapted viruses revealed no differences.

Three strains, RV-4, RV-5 and RV-6 formed plaques of varying sizes (0.25 mm–3.5 mm.) One strain, RV-3 produced plaques which consisted of thickening of cells similar to that described in 1982 by Faulkner-Valle et al ("Molecular biology of rotaviruses III. Isolation and characterization of temperature-sensitive mutants of bovine rotaviruses." J. Virol. 42:669–677) for a ts mutant of an animal rotavirus, instead of the usual areas of clearing of the cell monolayer. The remaining two strains, RV-1 and RV-2 could not be adapted to plaque formation. The titre of the strains that could be plaqued varied between $10^5$–$10^6$ infectious particles per ml.

In FIG. 2, plaque formation by human rotaviruses RV-5(B) and RV-3(C) is compared with uninfected cell control (A). Areas of clearing are noticeable in B and areas of thickening in C.

Human rotavirus RV-3 is known to belong to rotavirus subgroup 2 on the basis of gel electrophoresis of RNA genome, and to be serotype 3 on the basis of its reactions to polyclonal and monoclonal antibodies. RV-3 is also identified specifically by use of a monoclonal antibody developed in the Department of Gastroenterology, Royal Children's Hospital, Melbourne, Australia. This antibody is designated Mab RV-3:3 (previously designated 101AB5-B8). It reacts 1,000 times more strongly with RV-3 than with any other rotavirus tested.

RV-5 is known to belong to rotavirus subgroup 1 (by gel electrophoresis of RNA genome) and to be serotype 2 (by reaction to polyclonal and monoclonal antibodies). Part of the unique biochemical structure of RV-5 is now known, as described in Dyall-Smith M. L. and Holmes I. H., "Sequence homology between human and animal rotavirus serotype-specific glycoproteins". Nucleic Acids Research (1984), 12:109.

Preparation of vaccine

A preferred route for the preparation of the vaccine according to the invention follows current WHO standards for live poliomyelitis vaccine (oral), with appropriate modifications, "Requirements for poliomyelitis vaccine (oral)." WHO Expert Committee on Biological Standardization, 33rd Report, (Technical Report Series 687) pp. 107 to 74. WHO: Geneva; 1983.

Use of the vaccine

Initial oral vaccination is preferred before three months of age, preferably soon after birth, followed by a second vaccination three months later, when maternal antibody in infant serum has fallen to low levels. It appears that children are most vulnerable to severe clinical disease if infection occurs after this age. Although vaccination of the mother will provide a high titer of serum antibodies in the infant at birth, it is unlikely to protect against rotavirus infection after three months of age. The number of strains of rotavirus that are needed in an oral vaccine is not yet clear, but it is thought that infection by a single strain is sufficient to confer protection against severe disease caused by other strains.

However, a preferred vaccine comprises a suspension of one or several serotypes of live attenuated human rotavirus which has or have been grown in cultures of a human or monkey diploid cell strain. One or two doses of such vaccine would be administered by the oral route.

Deposit

A live attenuated strain of the virus designated Hu/Australia/10-25-10/77/L was deposited with the American Type Culture Collection (ATCC) on Feb. 1, 1985 and given the no. VR2104.

A live attenuated strain of the virus designated Hu/Australia/1-9-12/77/S was deposited with the ATCC on Feb. 1, 1985 and given the no. VR2105.

The claims defining the invention are as follows:

We claim:

1. A vaccine for providing immunological protection against acute diarrhea caused by human rotavirus, which comprises a live attenuated strain of the virus designated Hu/Australia/10-25-10/77/L ATCC number VR2104, in admixture with a suitable carrier.

2. A vaccine for providing immunological protection against acute diarrhea caused by human rotavirus, which comprises a live attenuated strain of the virus designated HU/Australia/1-9-12/77/S ATCC no. VR2105 in admixture with a suitable carrier.

3. A vaccine for providing enhanced immunological cross-protection against acute diarrhea caused by human rotavirus which comprises live attenuated strains of HU/Australia/1-9-12/77/S, ATCC no. VR2105 and HU/Australia/10-25-10/77/L, ATCC no. VR2104.

* * * * *